United States Patent [19]

Haas et al.

[11] Patent Number: 4,682,600

[45] Date of Patent: Jul. 28, 1987

[54] NON-INVASIVE METHOD AND APPARATUS FOR IN SITU DISINTEGRATION OF BODY CALCULI

[75] Inventors: Werner Haas, Uttenreuth; Wolfgang Knuepfer; Manfred Pfeiler, both of Erlangen, all of Fed. Rep. of Germany

[73] Assignee: Siemens Aktiengesellschaft, Berlin and Munich, Fed. Rep. of Germany

[21] Appl. No.: 750,141

[22] Filed: Jul. 1, 1985

[30] Foreign Application Priority Data

Jul. 13, 1984 [DE] Fed. Rep. of Germany ....... 3425897

[51] Int. Cl.⁴ .............................................. A61B 17/22
[52] U.S. Cl. .................................................... 128/328
[58] Field of Search ...................... 128/328, 24 A, 804

[56] References Cited

U.S. PATENT DOCUMENTS 3,077,195  2/1963  Folsche ................................ 128/804
4,003,383  1/1977  Brück .................................. 128/783
4,230,129  10/1980  LeVeen ................................ 128/804
4,526,168  7/1985  Hassler et al. ...................... 128/328

FOREIGN PATENT DOCUMENTS 0081639  6/1983  European Pat. Off. .
2508494  9/1976  Fed. Rep. of Germany ...... 128/804
2648908  5/1978  Fed. Rep. of Germany ...... 128/804
2718847  11/1978  Fed. Rep. of Germany ...... 128/804
3122056  12/1982  Fed. Rep. of Germany .

*Primary Examiner*—Lee S. Cohen
*Attorney, Agent, or Firm*—Hill, Van Santen, Steadman & Simpson

[57] ABSTRACT

A non-invasive method and apparatus for in situ disintegrating calculi in the body of a living being employ electromagnetic radiation generated by a transmission antenna. The electromagnetic radiation is highly focused at the location of the calculus to be disintegrated. The transmission antenna is matched to the body medium by a suitable dielectric material.

5 Claims, 2 Drawing Figures

NON-INVASIVE METHOD AND APPARATUS FOR IN SITU DISINTEGRATION OF BODY CALCULI

BACKGROUND OF THE INVENTION

1. Field of the Invention

The present invention relates to methods and devices for disintegrating calculi in the body, and in particular to a non-body invasive method and apparatus.

2. Description of the Prior Art

Disintegrating calculi, such as kidney stones, by means of ultrasonic shock waves is known, for example, from German OS No. 3122056. The existence of a boundary surface effect between body tissue and the stone structure is exploited. Reflection of the incident shock wave at the front or rear boundary surface of the calculus generates pressure or tensile forces which shortly result in the shattering of the calculus. In practice, coupling of the human body to a shock wave generator is undertaken by means of a water bath, which transmits the generated shock or pressure waves. This water bath also serves as a medium for removal of the ultrasonic energy which has passed by the stone region.

The use of such a water bath presents significant problems in patient support, as well as in monitoring the patient by means of a locating system, such as an X-ray system.

SUMMARY OF THE INVENTION

It is an object of the present invention to provide an apparatus and method for disintegrating calculi in the body which is non-body invasive.

The above object is inventively achieved by the use of a transmission antenna for generating an electromagnetic field which is highly focused and directed at the calculus to be disintegrated. As used herein, therefore, the terms 'electromagnetic field' and 'electromagnetic radiation' do not include those types of mechanical vibration wherein a series of pressure fronts or waves are developed, such as ultrasound. The transmission antenna is matched to the body medium by a suitable dielectric material, for example a ceramic compound. The polarization in the calculus to be disintegrated is constantly altered by means of this field, particularly by means of an alternating electromagnetic field. The magnitude of the force vector increases with increasing frequency in that region in which the linear extent of the calculus is smaller than the reciprocal of the frequency of the alternating field. The electrical forces thereby exerted on the calculus result in shattering or disintegration of the calculus by tensile stress. Because the calculus to be distintegrated has a finite conductivity in the alternating electromagnetic field, and currents are induced in the calculus, magnetic forces, which also contribute to disintegration, arise. When disintegrating kidney stones, for example, tensile forces have the advantage that they can be of approximately one order of magnitude lower than compressive forces in order to achieve the same shattering effect. In contrast to the calculus to be disintegrated, the soft body tissue of the patient surrounding the calculus represents a far more homogenous structure with respect to electromagnetic radiation than the same tissue does for an ultrasonic shock wave. Unintentional injury to surrounding body structures having pronounced boundary surfaces, for example bones, is therefore less probable utilizing electromagnetic radiation than in conventional devices making use of ultrasonic shock waves. By focusing the electromagnetic radiation over a significant part of the body periphery onto the calculus, forces are generated not only at the boundary surfaces thereof, but also heat is generated in the interior thereof, the heat promoting disintegration of the calculus.

DESCRIPTION OF THE PREFERRED EMBODIMENTS

Figure 1:
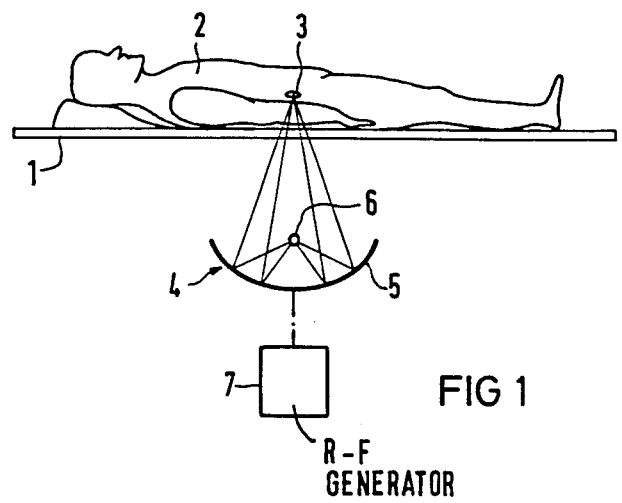
FIG. 1 is a side view of an apparatus for disintegrating calculi constructed in accordance with the principles of the present invention and practicing the method disclosed herein.

A patient support 1 is shown in FIG. 1 on which a patient 2 rests. The patient has a calculus 3, for example a kidney stone. A transmission antenna 4 is provided for disintegrating or shattering the calculus 3. The antenna 4 has a transmitter 6 disposed at the focus of a concave mirror 5 for generating an electromagnetic field, such as an alternating electromagnetic field. The electromagnetic radiation emitted by the transmitter 6 are focused onto the calculus 3 by proper and selected orientation of the patient 2 on the patient support 1 relative to the transmission antenna 4. The transmitter 6 is fed by a radio frequency generator 7.

Another embodiment of the method and apparatus disclosed herein is shown in FIG. 2, wherein again a patient 2 having a calculus 3 rests on a patient support 1. In this embodiment, the patient 2 is surrounded by an array of individual antenna elements 8 with suitable dielectric matching to the body medium such as by means of a ceramic compound schematically represented at 8a. The antenna elements 8 are aligned so as to individually direct the emitted radiation at the calculus 3, this again being achieved by a proper orientation of the support 1 for the patient 2. The individual feed of the antenna elements 8 is undertaken by a radio frequency generator 7a.

The transmission antennae 4 and 8, and the radio frequency generators 7 and 7a, may be designed for emitting radiation having a broad frequency spectrum. The radiation may be in the form of radio frequency pulses having spectral emphasis in an optimum region. This optimum frequency region is determined by calculating the increase in the action of the generated forces and the corresponding decrease in the penetration depth which is associated with each frequency.

Figure 2:
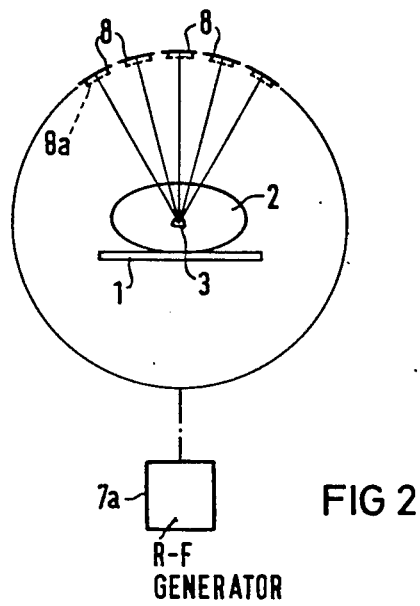
FIG. 2 is an end view of another embodiment of a apparatus for disintegrating calculi constructed in accordance with the principles of the present invention and practicing the method disclosed herein.

In the embodiment of FIG. 2, the antenna elements 8 may be horn radiators, rectangular waveguides, or other types of discrete radiating antennae known to those skilled in the art.

Although modifications and changes may be suggested by those skilled in the art, it is the intention of the inventors to embody within the patent warranted herein all changes and modifications as reasonably and properly come within the scope of their contribution to the art.

We claim as our invention:

1. A method for non-body invasive disintegration of a calculus in the body of a patient comprising the steps of:
   supporting the patient on a patient support bed;
   generating electromagnetic radiation; and focusing said electromagnetic radiation at said calculus in said patient.

2. A method as claimed in claim 1 wherein the step of generating said electromagnetic radiation is further defined by generating electromagnetic radiation by means of a transmission element disposed at the focus of a concave reflector, said concave reflector being shaped for directing the reflected electromagnetic radiation at said calculus.

3. A method as claimed in claim 1 wherein said electromagnetic radiation is generated at a source, and wherein the step of focusing said electromagnetic radiation at said calculus is further defined by orienting said patient support bed with respect to said source for directing said electromagnetic radiation at said calculus.

4. A method as claimed in claim 1 wherein the step of generating said electromagnetic radiation is further defined by generating electromagnetic radiation from a plurality of discrete radiating elements disposed in an array around said patient.

5. A method as claimed in claim 1 comprising the additional steps of pulsing said electromagnetic radiation.

* * * * *